United States Patent [19]
Shishov et al.
[11] Patent Number: 4,645,487
[45] Date of Patent: Feb. 24, 1987

[54] DEVICE FOR ADMINISTERING POWDERED SUBSTANCES

[75] Inventors: Nikolai M. Shishov; Vladimir E. Zelenetsky; Nadezhda A. Demina; Ivan M. Bondarev; Alexandr N. Cherny, all of Moscow; Anatoly G. Avxentiev, Belgorod-Dnestrovsky; Evgeny E. Rylov, deceased, late of Moscow, all of U.S.S.R., by Nina A. Rybakova, administratrix

[73] Assignee: Vsesojuzny Nauchno-Issledovatelsky Institut*, Moscow, U.S.S.R.

[21] Appl. No.: 617,507

[22] Filed: Jun. 5, 1984

[51] Int. Cl.[4] .......... A61M 13/00
[52] U.S. Cl. .......... 604/58; 222/325; 169/33
[58] Field of Search .......... 604/58, 27, 36, 38; 128/203.15; 222/490, 325, 209; 169/33

[56] References Cited

U.S. PATENT DOCUMENTS

| | | | |
|---|---|---|---|
| 2,518,522 | 8/1950 | Cimbura et al. | 222/325 |
| 2,518,523 | 8/1950 | Cimbura et al. | 222/325 |
| 2,525,742 | 10/1950 | Weiss et al. | 169/33 |
| 2,946,332 | 7/1960 | Sacks | 128/203.15 |
| 3,093,274 | 6/1963 | Galbierz | 222/325 |
| 3,858,583 | 1/1975 | Hallworth | 128/203.15 |
| 3,906,950 | 9/1975 | Cocoza | 128/203.15 |
| 3,949,751 | 4/1976 | Birch et al. | 128/266 |
| 4,017,007 | 4/1977 | Riccio | 604/58 |
| 4,082,095 | 4/1978 | Mendelson | 604/38 |

FOREIGN PATENT DOCUMENTS

| | | | |
|---|---|---|---|
| 607237 | 8/1948 | United Kingdom | 604/58 |
| 1436028 | 5/1976 | United Kingdom . | |
| 615934 | 7/1978 | U.S.S.R. . | |

OTHER PUBLICATIONS

I. M. Bondareva, L. I. Zhigalina, A. N. Chernyi, Device for Administering Medicinal Substance into Human Organism, Meditsinskaya tekhnika—Journal of Medical Technology, No. 6, 1976, Moscow, pp. 17–18.

*Primary Examiner*—Anton O. Oechsle
*Assistant Examiner*—T. Brown
*Attorney, Agent, or Firm*—Fleit, Jacobson, Cohn & Price

[57] ABSTRACT

The device includes a sprayer of powdered substances having a conveying line which includes a coaxially arranged drain pipe and a catheter. The sprayer includes a piston with a valve and a cylindrical housing having a valve and a diametral partition with an opening. The partition divides the sprayer into a delivery portion and a spraying portion.

8 Claims, 4 Drawing Figures

DEVICE FOR ADMINISTERING POWDERED SUBSTANCES

TECHNICAL FIELD

This invention relates to surgical devices and, more particularly, it relates to devices for administering powdered substances.

The present invention may be used for administering medicinal substances into human organism, in particular, into deepseated cavities of the organism. This invention may be used most advantageously in treating cavernous forms of tuberculosis, however, it may also be employed for treating a residual postresection cavity in the pleura or the empyema of the chest, or when giving emergency aid to spontaneous pneumothorax patients.

BACKGROUND OF THE INVENTION

There is known in the art a device for administering powdered medicine into the body of a patient (cf., British Pat. No. 1,436,028, index of acceptance A 5R33E).

Said prior art device comprises a chamber with a capsule of medicine accommodated therein and two coaxially arranged pipes connected to the capsule, one of said pipes being connected with a bottle for the delivery of air to the capsule while the other one of the pipes serves for injecting the powdered medicine into the patient's body cavity via mouth, nose, ears, through damaged tissue or wounds.

However, the structure of said prior art device does not permit of percutaneous administration of powdered substances into deep-seated cavities of the organism such as tuberculous cavern cavity.

Another prior art device for administering powdered medicine into human organism comprises a container for medicinal preparation connected with a rubber bottle, and a pipeline connected with a metal trocar and catheter. In so doing, the trocar and catheter are arranged coaxially, with a clearance therebetween (cf., I. M. Bondareva, L. I. Zhigalina, A. N. Chernyi, Device for Administering Medicinal Substance Into Human Organism, Meditsinskaya tekhnika—Journal of Medical Technology, No. 6, 1976, Moscow, pp. 17–18).

In the course of treatment, the skin and underlying tissues are punctured with the metal trocar including a tight-fitting stylet terminating in a piercing point. After that, the stylet is withdrawn from the trocar and replaced with a rigid catheter. The process of administering the medicinal preparation is performed from the container via catheter owing to an air pulse obtained upon compression of the rubber bottle. Excess air is removed from the focus of disease via clearance between the trocar and catheter walls and further via union located in the proximal portion of the trocar.

This latter prior art device suffers from the following disadvantages:

the metal trocar is introduced into one and the same spot of the patient's body each time the preparation is administered (every 2–3 days throughout the entire period of the course of treatment which may last for at least 6 months), this causing strong painful sensations;

in addition, the introduction of metal trocar into the organism is always accompanied with X-ray treatment, which causes an increase in the irradiation dose received by the patient and personnel throughout the course of treatment;

in its proximal portion, the trocar is made fast in a head with union, said head being provided with a groove for receiving a pin designed to fix the stylet in a preset position, which complicates the trocar structure;

the removal of bacteria-contaminated excess air from the focus of disease via union directly to the environment appears undesirable because the personnel may get the infection;

because of the device structure, the pipeline cannot be tightly joined with the catheter, which causes the formation of powder settling zones and the plugging of the catheter.

Besides that, the currently employed technology of manufacturing metal needles does not permit of attaining a higher grade of the required roughness of the needle inner surface, which is likewise conducive to the plugging of the catheter with powder.

There is known a pulverizer of powdered substances, which comprises a hermetic cone-shaped glass container for powdered substance sealed at straight angles in a pipeline and connected with delivery means fashioned as a rubber bulb provided with an additional chamber. The narrow portion of the coneshaped container has double walls with a space therebetween. The inner wall is provided with capillary openings while the space between the walls is connected to the additional chamber of the rubber bulb (cf., U.S.S.R. Inventor's Certificate No. 615,934, Int.Cl.$^2$ A 61 M 11/02, of 1978).

The disadvantages of said prior art device reside in complicated structure and technology of manufacturing the powder container and delivery means. Because of this design, every individual device is to be manufactured manually. The manufacturing process is not susceptible to automation or mechanization.

In view of the absence of valves in the delivery means, the pipeline may be plugged with powder due to the emergence of return air flow.

The powder may be drawn in connecting elements and delivery means and can only be removed after disassembling the entire device and cleaning its parts, which complicates the work of the medical personnel.

Moreover, such a pulverizer design is characterized by the possibility of frequent clogging of the pipeline with powder which affects the efficiency of pulverization and reliability of operation because, upon compression of the rubber bulb, part of the air flow supplied to the container from the smaller chamber transfers a small amount of powder to the pipeline where said powder is condensed by the air flow supplied from the bigger chamber of the bulb and moved via pipeline to the cavern.

There is further known a device for administering medicine to human organism, which comprises a housing accommodating therein a capsule with medicine, one end of the housing being connected with air delivery means in the form of a rubber bottle with a built-in unidirectional valve accommodating thereinside a needle for puncturing the medicine capsule while the other end of the housing is connected with a detachable tip for the injection of powder (cf., U.S. Pat. No. 3,949,751, class 128-266, of 1976).

When using said latter prior art device, the capsule with medicinal preparation is placed inside the housing and the latter is coupled with the detachable tip and delivery means. The rubber bottle is squeezed in the longitudinal direction: both end walls of the capsule are punctured by the needle. For pulverizing the medicinal preparation, the bottle is squeezed in the lateral direction. The air passes both inside and outside of the capsule.

Upon return of the bottle to its initial shape, the valve is opened and air is supplied to the bottle.

However, said prior art device suffers from a number of disadvantages.

The misalignment of the capsule and housing space results in a nonuniform flow of air around the capsule and, consequently, in a decrease of the uniformity of powder distribution in the air flow and of pulverization efficiency.

The provision of two holes in the capsule affects the pulverization efficiency because the air supplied to the capsule compacts the powder at the outlet hole. In addition, the puncturing of the end walls of the capsule is accompanied with the formation of burrs on which powdered medicine tends to accumulate upon return air flow, said burrs also facilitating the clogging of the holes, which likewise affects the efficiency of administering the medicine.

The provision of a single unidirectional valve does not rule out the possibility of return suction of medicinal preparation into the housing space and into the chamber located near the inlet hole, which may lead to the clogging of the capsule holes, especially, when spraying the powder in deep-seated cavities of the organism.

Therefore, said latter prior art device fails to provide for reliable operation at the moment of spraying the powder in a deep-seated cavity of the organism and, at the same time, attain a uniform and efficient pulverization of medicinal preparation.

BRIEF DESCRIPTION OF THE INVENTION

It is an object of the present invention to provide a device for administering powdered substances, the use of which would help reduce the overall duration of treatment by ensuring the possibility of repeated connection of the device to a drain pipe without removing the drain pipe from the patient's body throughout the course of treatment.

It is another object of this invention to accelerate the spraying process by improving the uniformity of distribution of powdered substance in a jet of spraying gas.

It is yet another object of the invention to provide a device free of clogging of the conveying line with powdered substance.

It is a further object of this invention to provide a device wherein no powder would be returned to the sprayer.

It is one more object of the present invention to simplify the device structure and increase the reliability of its operation.

The objects set are attained in a device for administering powdered substances into deep-seated cavities of human organism, comprising series-connected sprayer and conveying line including coaxially arranged drainage pipe and catheter, wherein, according to the present invention, the sprayer includes a piston with a valve and a cylindrical housing having a valve and a diametral partition with an opening, said partition dividing the sprayer into a delivery portion and a spraying portion in which a container with powdered substance being sprayed is mounted with a clearance, said container having one opening directed towards the conveying line coaxial with the container and connected to the spraying portion.

It is expedient that the piston should have ribs in the form of longitudinal cross-shaped plates which may have a piston arrester attached thereon, while the valve may be mounted on the piston end facing the diametral partition of the cylindrical housing of the sprayer means.

The spraying portion of the sprayer may be fashioned as a diffuser whose inner surface is analogous with the outer surface of the container with powdered substance being sprayed and provided with longitudinal ribs.

It is desirable that the piston arrester be fashioned as two half-disks with a recess and a projection on their end face.

For connecting the catheter to the outlet opening of the spraying portion of the sprayer, the catheter may have a flared end.

For a possibility of its repeated use, the container with powdered substance being sprayed may have a detachable sealed cover.

The herein disclosed device for administering powdered substances into the patient's organism makes for a considerable reduction of the overall duration of treatment and provides a possibility of its repeated connection to the patient's body without performing any additional operations, without removing from the patient's body a drain pipe tube introduced the first time the medicinal substance is administered.

Further, the medicine is administered in uniform doses effectively sprayed in the organism cavity to provide for a more rapid recovery of patients.

Powdered medicinal substance does not accumulate in spaces of the device, thereby facilitating considerably the device operation and improving its reliability.

The device is simple and readily adaptable to manufacture, especially, when employing polymeric materials.

BRIEF DESCRIPTION OF DRAWINGS

Other objects and advantages of the present invention will be made apparent upon considering the following detailed description of examplary embodiments thereof, with due reference to the accompanying drawings, wherein.

DETAILED DESCRIPTION OF THE INVENTION

Figure 4:
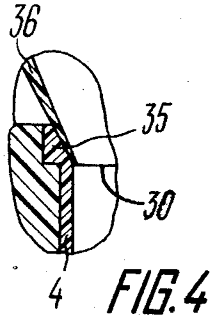
FIG. 4—ditto, a scaled-up view of the portion where the catheter is mounted.

Referring now to the accompanying drawings, the herein disclosed device for administering powdered substances into deep-seated cavities of the patient's organism comprises, connected in series, a sprayer 1 (FIG. 1) and a conveying line 2 including a drainage pipe 3 and a catheter 4 arranged coaxially with each other. The sprayer 1 includes a piston 5 (FIG. 2) and a cylindrical housing 6.

The cylindrical housing 6 accommodates therein a diametral partition 7 with an opening 8, said partition dividing the sprayer into a delivery portion 9 and a spraying portion 10.

The piston 5 has a valve mounted on an end face of the piston 5 on the side facing the diametral partition 7. The valve includes a disk-type polymeric membrane 11 loose-fitted in a recess of the piston 5 and a cylindrical insert 12 having on its outer surface longitudinal ribs 13 resting against a circular projection 14 in the piston recess, said insert developing a gap for the passage of gas from the piston 5 to the cylindrical housing 6. Air intake holes 15 are provided in the bottom of the piston 5.

Figure 3:
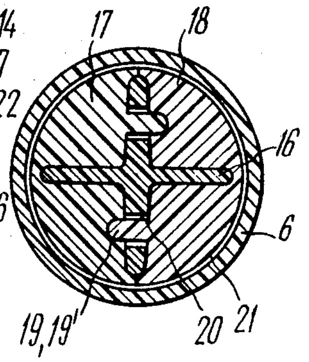
FIG. 3—ditto, a section taken along line III—III of FIG. 2.

Provided on the body of the piston 5 are ribs 16 (FIG. 3) in the form of longitudinal cross-shaped plates, to which ribs 16 there is attached a piston arrester fashioned as two half-disks 17 and 18. On the opposing end faces of the half-disks 17 and 18 there are provided a recess 19 and a corresponding tapered projection 19' for securing the half-disks 17 and 18 to each other.

Holes 20 are provided in the portions where the half-disks 17 and 18 are secured to the ribs 16. The half-disks 17 and 18 are installed in the housing 6 with a clearance 21.

Mounted in the spraying portion 10 (FIG. 2) of the sprayer near the partition 7 is another valve including a body 22 with a central opening 23 in its bottom, said opening covered with a polymeric membrane 24 urged by a polymeric spring 25. The latter valve is secured in position in the housing 6 by means of a circular projection 26.

The spraying portion 10 comprises an auxiliary housing 27 which has a cylindrical portion 28 and a tapered portion 29 terminating in an outlet opening 30 and forming a diffusor. The housing 27 accommodates therein a container 31 with powdered substance being sprayed having an opening 32 directed towards the conveying line 2 (FIG. 1).

The outer surface of the container 31 (FIG. 2) is analogous with the inner surface of the housing 27 while the inner surface of the container has a smooth outline and rules out the possibility of the formation of stagnant pockets upon spraying of the powdered substance. The container 31 is mounted in position in the housing 27 with a clearance by means of longitudinal ribs 33 provided on the inner surface of the housing 27. The container 31 may be employed for one application, however, it is expedient that the container 31 should be adapted for repeated use by providing it with a detachable sealed cover 34.

Figure 1:
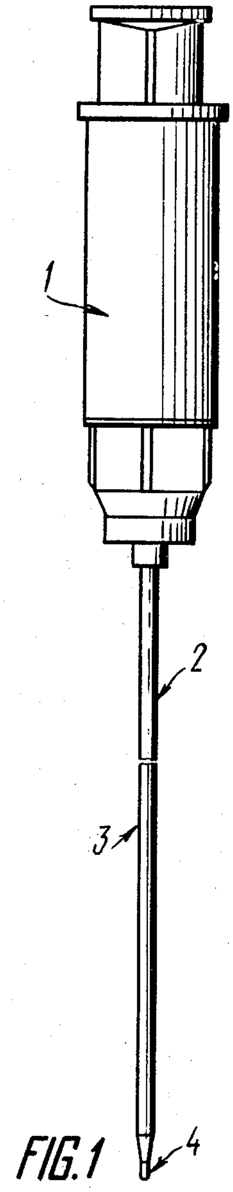
FIG. 1 is a general view of the device for administering powdered substances, according to the present invention.
Figure 2:
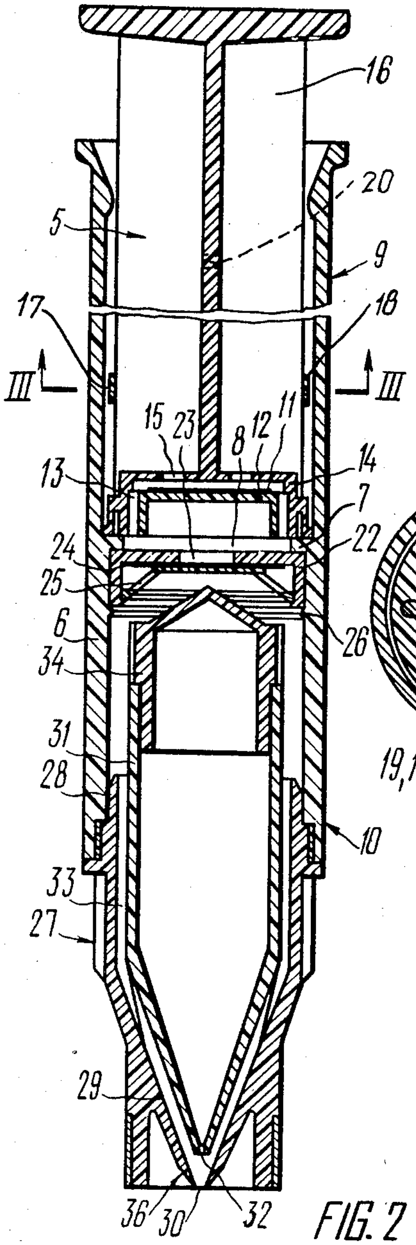
FIG. 2 shows a sprayer according to the present invention, in longitudinal section.

The opening 32 of the container 31 and the opening 30 in the housing 27 are coaxial with the conveying line 2 (FIG. 1).

The ribs 33 (FIG. 2) on the housing 27 ensure a guaranteed clearance between the openings 30 and 32.

The spraying portion 10 is communicated with the conveying line 2 (FIG. 1).

For precluding the formation of stagnant pockets of powder at the time of spraying, the catheter 4 has a flared end 35 (FIG. 4) ensuring a tight coupling of an outlet end 36 (FIG. 4) of the spraying portion 10 (FIG. 2) of the sprayer with the catheter 4.

The herein disclosed device for administering powdered substances operates in the following manner.

The pipe 3 is introduced with the aid of a hollow stylet and under X-raying into the cavity of tubercular cavern and mounted in the patient's body for the entire duration of the course of treatment with the aid of any suitable fixation means (not shown in the drawings).

The stylet structure enables one to perform trial aspiration of the destructive cavity of the cavern of the lung at the moment of introduction of the pipe 3 owing to the connection of the stylet to vacuum suction means.

The requisite amount of powdered substance is poured into the container 31, the container is closed tightly with the cover 34 and placed in the housing 27. The housing 27 is threaded to the cylindrical housing 6 of the sprayer. Then, the catheter 4 is connected to the spraying portion 10. The half-disks 17 and 18 of the piston arrester are made fast in the holes on the ribs of the piston 5 in a certain position, depending on the size of the cavern of the lung.

Prior to the spraying of powder, the catheter 4, connected to the sprayer 1, is inserted into the pipe 3. Thereupon, the piston 5 is moved to the topmost position for effecting the intake of air to the delivery portion 9 of the delivery means. While so doing, air is supplied via holes 15, presses out the membrane 11 and passes through grooves between the ribs 13 of the cylindrical insert 12.

At this time, the other valve facing the diametral partition 7 is closed, i.e., the membrane 24 closes the opening 23, this preventing the powdered substance from returning together with air from a cavern cavity into the conveying line 2 and, consequently, from clogging the latter.

After that, the piston 5 is moved to the lowermost position, with the holes 15 being closed by the membrane 11 under the effect of compressed air while the opening 23 is opened owing to the compression of the spring 25. Thereupon, air flows at a high rate about the container 31 with powdered substance to capture part of the substance from the container 31 owing to rarefaction developed at the outlet end 30 and move said substance along the catheter to the cavity of tubercular cavern.

The cycle of delivering the powdered substance may be repeated many times over until all of the substance from the container 31 is injected into the cavern cavity.

Upon completion of the procedure spraying, the catheter 4 with sprayer is removed from the pipe 3, and the used container 31 is removed from the device and the housing 27 is disconnected from the cylindrical housing 6 of sprayer.

The herein disclosed device for administering powdered substances into the patient's organism is noted for the following advantages.

All of the parts and assemblies of the device of the invention are such that they can be made from polymeric material; they are readily adaptable to manufacture, thereby rendering their manufacture simpler and obviating junctions between parts that might cause the sticking of powder and clogging of the conveying line.

The device of the invention increases the spraying efficiency because the provision of ribs on the inner surface of the sprayer makes it possible to position the container with powdered substance coaxially with the housing, thereby ensuring a guaranteed circular clearance between the container and sprayer housing and between the openings of the sprayer housing and container in the axial direction at the end of narrowing. Such an arrangement of the container provides for a uniform flow of air around said container, which results in a uniform distribution of powder in the air flow and makes for better flowability of the medicinal preparation.

The spraying efficiency is further increased owing to the provision in the container of only one central opening at the end of narrowing of the container.

The device structure provides for its repeated use during the course of treatment of single patient and provides the possibility of daily administration of powdered substance.

The patient is saved from repeated surgical traumas caused by puncturing the tissues; the overall dose of X-ray irradiation is reduced; the possibility of personnel getting infected is ruled out.

The reliability of the device operation is improved by the provision in the sprayer of two unidirectional valves for the supply of gas, precluding the possibility of return air flow.

The herein disclosed device for administering powdered medicinal substance into the patient's organism, in particular, into the cavity of tubercular cavern, will help sharply increase the efficiency of treating patients suffering from cavernous tuberculosis, reduce the time of treatment and the patients' stay in hospital and, therefore, reduce the cost of treatment, speed up the recovery of patients to useful activities and to preclude the emergence of new cases of tuberculosis.

What is claimed is:

1. A device for administering powdered substances into deep-seated cavities of a patient's organism, said device comprising:

- a sprayer for spraying a powdered substance,
- a conveying line series-connected to said sprayer, said conveying line including a drain pipe and a catheter arranged coaxially inside of said drain pipe and adapted to be introduced into a deep-seated cavity of the patient's organism for spraying the powdered substance therein;
- said sprayer including
  - a cylindrical housing;
  - a diametral partition located in said cylindrical housing and having a first opening;
  - said diametral partition dividing said cylindrical housing into a delivery portion and a spraying portion having an outlet opening;
  - a piston located in said cylindrical housing being movable up and down along said cylindrical housing;
  - a first valve mounted in said cylindrical housing; and
  - a second valve mounted on said piston;
  - a container for containing the powdered substance to be sprayed;
  - said container mounted within said cylindrical housing and being spaced from said cylindrical housing to define a clearance;
  - a second opening provided in said container and directed, upon mounting said container in said spraying portion, towards said conveying line, said second opening being coaxial with said conveying line for the delivery of powdered substance being sprayed to said catheter due to rarefaction developed at the outlet end of the sprayer.

2. A device as set forth in claim 1, further comprising ribs in the form of cross-shaped longitudinal plates provided on said piston of said sprayer, and a piston arrester attached to said ribs.

3. A device as set forth in claim 2, wherein said piston arrester comprises a first half-disk and a second half-disk identical with each other, at least one recess defined by said first half-disk and said second half-disk, at least one projection defined by said first half-disk and said second half-disk, the number of said projections corresponding to the number of said recesses, said recesses and said projections engaging each other to provide a rigid connection of said first half-disk and said second half-disk.

4. A device as set forth in claim 1, wherein said second valve is mounted on said piston end facing said diametral partition of said cylindrical housing of said sprayer.

5. A device as set forth in claim 1, wherein said spraying portion includes an inner surface spaced from an exterior surface of said container, and longitudinal ribs are attached to said inner surface to define said clearance between said container and said inner surface while accommodating said container in said spraying portion.

6. A device as set forth in claim 5, wherein said container for the powdered substance to be sprayed has a detachable sealed cover ensuring repeated use of said container.

7. A device as set forth in claim 1, wherein said catheter has one of its ends flared and connected to said outlet opening of said spraying portion of said sprayer.

8. A device for administering powdered substances into deep-seated cavities of a patient's organism, said device comprising:

- a sprayer for spraying a powdered substance,
- a conveying line series-connected to said sprayer, said conveying line including a drain pipe and a catheter arranged coaxially inside of said drain pipe and adapted to be introduced into a deep-seated cavity of the patient's organism for spraying the powdered substance therein;
- said catheter having one of its ends flared;
- said sprayer including
  - a cylindrical housing;
  - a diametral partition located in said cylindrical housing and having a first opening;
  - said diametral partition dividing said cylindrical housing into a delivery portion and a spraying portion provided with an outlet opening and longitudinal ribs attached to said cylindrical housing inside said spraying portion;
  - said flared end of said catheter being coupled to said outlet opening of said spraying portion;
  - a piston located in said cylindrical housing being movable up and down along said cylindrical housing and having ribs in the form of cross-shaped longitudinal plates;
- a piston arrester attached to said ribs;
  - a first valve mounted in said cylindrical housing;
  - a second valve mounted on said piston end facing said diametral partition;
  - said piston arrester including a first half-disk and a second half-disk identical with each other, at least one recess defined by said first half-disk and said second half-disk, at least one projection defined by said first half-disk and said second half-disk, the number of said projections corresponding to the number of said recesses, said projections engaging said recesses to form a rigid connection of said first half-disk and said second half-disk; and
  - a container for containing the powdered substance to be sprayed;
  - said container having a shape corresponding to that of said inner surface of said spraying portion and mounted in said spraying portion spaced from said cylindrical housing to define a clearance between said inner surface of said spraying portion and said container.

* * * * *